US00PP21638P2

(12) United States Plant Patent
Dümmen

(10) Patent No.: US PP21,638 P2
(45) Date of Patent: Jan. 18, 2011

(54) ***VERBENA* PLANT NAMED 'DUEMPLAVBU'**
(50) Latin Name: *Verbena hybrida*
Varietal Denomination: Duemplavbu

(75) Inventor: Tobias Dümmen, Rheinberg (DE)

(73) Assignee: Capital Green Investments Ltd., Grand Cayman (KY)

( * ) Notice: Subject to any disclaimer, the term of this patent is extended or adjusted under 35 U.S.C. 154(b) by 0 days.

(21) Appl. No.: 12/587,115

(22) Filed: Oct. 1, 2009

(51) Int. Cl.
*A01H 5/00* (2006.01)

(52) U.S. Cl. ..... Plt./308
(58) Field of Classification Search ..... Plt./308

See application file for complete search history.

*Primary Examiner*—Susan B McCormick Ewoldt
(74) *Attorney, Agent, or Firm*—C. A. Whealy

(57) ABSTRACT

A new and distinct cultivar of *Verbena* plant named 'Duemplavbu', characterized by its semi-upright, compact and mounded plant habit; freely branching habit; freely flowering habit; and large purple violet-colored flowers that are held above and beyond the foliage in mounded umbels.

1 Drawing Sheet

Botanical designation: *Verbena hybrida.*
Cultivar denomination: 'DUEMPLAVBU'.

BACKGROUND OF THE INVENTION

The present invention relates to a new and distinct cultivar of *Verbena* plant, botanically known as *Verbena hybrida,* and hereinafter referred to by the name 'Duemplavbu'.

The new *Verbena* plant is a product of a planned breeding program conducted by the Inventor in Rheinberg, Germany. The objective of the breeding program is to create new semi-upright and compact *Verbena* plants with numerous attractive flowers.

The new *Verbena* plant originated from a cross-pollination made by the Inventor in July, 2007 in Rheinberg, Germany of a proprietary selection of *Verbena hybrida* identified as code number V05-4230-001, not patented, as the female, or seed, parent with a proprietary selection of *Verbena hybrida* identified as code number V05-3199-001, not patented, as the male, or pollen, parent. The new *Verbena* plant was discovered and selected by the Inventor as a single flowering plant within the progeny of the stated cross-pollination in a controlled greenhouse environment in Rheinberg, Germany in May, 2009.

Asexual reproduction of the new *Verbena* plant by terminal cuttings in a controlled greenhouse environment in Rheinberg, Germany since May, 2009 has shown that the unique features of this new *Verbena* plant are stable and reproduced true to type in successive generations.

SUMMARY OF THE INVENTION

Plants of the new *Verbena* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Duemplavbu'. These characteristics in combination distinguish 'Duemplavbu' as a new and distinct cultivar of *Verbena:*

1. Semi-upright, compact and mounded plant habit.

2. Freely branching habit.
3. Freely flowering habit.
4. Large purple violet-colored flowers that are held above and beyond the foliage in mounded umbels.

Plants of the new *Verbena* differ primarily from plants of the parent selections in flower color as plants of the parent selections have red-colored flowers. In addition, plants of the new *Verbena* are more compact than plants of the male parent selection.

Plants of the new *Verbena* can be compared to plants of the *Verbena hybrida* 'Duplena', disclosed in U.S. Plant Pat. No. 15,687. In side-by-side comparisons conducted in Rheinberg, Germany, plants of the new *Verbena* differed from plants of 'Duplena' in the following characteristics:

1. Plants of the new *Verbena* were more compact than plants of 'Duplena'.
2. Plants of the new *Verbena* had shorter internodes than plants of 'Duplena'.
3. Plants of the new *Verbena* had smaller leaves than plants of 'Duplena'.

BRIEF DESCRIPTION OF THE PHOTOGRAPH

The accompanying colored photograph illustrates the overall appearance of the new *Verbena* plant, showing the colors as true as it is reasonably possible to obtain in colored reproductions of this type. Colors in the photograph may differ slightly from the color values cited in the detailed botanical description which accurately describe the colors of the new *Verbena* plant. The photograph comprises a close-up view of typical leaves and inflorescences of 'Duemplavbu'.

DETAILED BOTANICAL DESCRIPTION

The aforementioned photograph and following observations, measurements and values describe plants grown in 10.5-cm containers in Rheinberg, Germany in a glass-covered greenhouse during the summer and under conditions which closely approximate commercial production. During the production of the plants, day and night temperatures averaged 18° C. and light levels averaged 4,500 lux. Plants were pinched one time three weeks after planting. Plants were ten weeks old when the photograph and the description were taken. In the description, color references are made to The Royal Horticultural Society Colour Chart, 2001 Edition, except where general terms of ordinary dictionary significance are used.

Botanical classification: *Verbena hybrida* 'Duemplavbu'.

Parentage:

*Female, or seed, parent.*—Proprietary selection of *Verbena hybrida* identified as code number V05-4230-001, not patented.

*Male, or pollen, parent.*—Proprietary selection of *Verbena hybrida* identified as code number V05-3199-001, not patented.

Propagation:

*Type.*—Terminal cuttings.

*Time to initiate roots, summer.*—About five days at 20° C.

*Time to initiate roots, winter.*—About seven days at 20° C.

*Time to produce a rooted young plant, summer.*—About three weeks at 20° C.

*Time to produce a rooted young plant, winter.*—About four weeks at 20° C.

*Root description.*—Fine, fibrous; white in color.

*Rooting habit.*—Freely branching; dense.

Plant description:

*Plant habit.*—Semi-upright, compact and mounded plant habit; freely branching habit with about four to six primary lateral branches with secondary lateral branches potentially forming at every node; pinching enhances lateral branch development; dense and bushy plant habit; moderately vigorous growth habit.

*Plant height.*—About 16 cm.

*Plant diameter.*—About 20 cm.

Lateral branch description:

*Length.*—About 15 cm.

*Diameter.*—About 2.5 mm.

*Internode length.*—About 1.8 cm.

*Texture.*—Pubescent.

*Strength.*—Strong.

*Color.*—Close to 144A.

Foliage description:

*Arrangement.*—Opposite, simple.

*Length.*—About 3.6 cm.

*Width.*—About 2.3 cm.

*Shape.*—Lanceolate.

*Apex.*—Acute.

*Base.*—Attenuate.

*Margin.*—Lobed.

*Texture, upper and lower surfaces.*—Pubescent, coarse.

*Venation pattern.*—Pinnate.

*Color.*—Developing leaves, upper surface: Close to 137A. Developing leaves, lower surface: Close to 143A. Fully expanded leaves, upper surface: Close to 147A; venation, close to 144C. Fully expanded leaves, lower surface: Close to 137A to 137B; venation, close to 144B to 144C.

*Petiole length.*—About 2.4 mm.

*Petiole diameter.*—About 2.4 mm.

*Petiole texture, upper and lower surfaces.*—Smooth.

*Petiole color, upper surface.*—Close to 144A.

*Petiole color, lower surface.*—Close to 144B.

Flower description:

*Flower arrangement and habit.*—Salverform flowers arranged in hemispherical terminal umbels; umbels dense and mounding; numerous umbels covering the entire plant; flowers face upward or outward; freely flowering habit with about 20 flowers and flower buds per inflorescence.

*Fragrance.*—Flowers not fragrant.

*Natural flowering season.*—Plants flower continuously from the spring through the fall in Germany; plants begin flowering about eight weeks after planting.

*Flower longevity.*—Individual flowers last about one week on the plant; flowers persistent.

*Inflorescence size.*—Height: About 3.5 cm. Diameter: About 5.5 cm.

*Flowers.*—Appearance: Flared trumpet, corolla fused, five-parted. Diameter: About 2.2 cm. Depth: About 2.7 cm.

*Flower buds.*—Length: About 1.3 cm. Diameter: About 2.5 mm. Shape: Oval, tubular. Color: Close to 146A.

*Corolla.*—Arrangement: Single whorl of five fused petals. Petal lobe length: About 1.1 cm. Petal lobe width: About 1.1 cm. Petal lobe shape: Obovate. Petal lobe apex: Emarginate. Petal margin: Entire. Petal texture, upper and lower surfaces: Smooth, glabrous; velvety. Color: When opening, upper surface: Close to 82B. When opening, lower surface: Close to 82C to 82D. Fully opened, upper surface: Close to 82B; color becoming closer to 82A and 96B with development. Fully opened, lower surface: Close to 82C.

*Calyx.*—Arrangement: Star-shaped calyx with five fused sepals. Sepal length: About 1.3 cm. Sepal width: About 1.5 mm. Sepal shape: Ligulate. Sepal apex: Acute. Sepal margin: Entire. Sepal texture, upper and lower surfaces: Pubescent, coarse. Sepal color, upper and lower surfaces: Between 146A and 144A.

*Peduncles.*—Length: About 5 cm. Diameter: About 2.5 mm. Strength: Strong. Texture: Pubescent. Color: Close to 144A.

*Pedicels.*—Length: About 0.5 mm. Diameter: About 0.5 mm. Strength: Strong. Texture: Smooth, glabrous. Color: Close to 144A.

*Reproductive organs.*—Stamens: Quantity/arrangement: About four to five per flower, adnate to corolla tube. Anther shape: Oval. Anther length: About 0.75 mm. Anther color: Close to 144B. Pollen amount: Moderate. Pollen color: Close to 2D. Pistils: Quantity: One per flower. Pistil length: About 1.7 cm. Stigma shape: Bi-parted. Stigma color: Close to 144A. Style length: About 1.6 cm. Style color: Close to 144D. Ovary color: Close to 144C. Fruits/seeds: Fruit and seed development has not been observed.

Temperature tolerance: Plants of the new *Verbena* have been observed to tolerate temperatures from about 5° C. to about 35° C.

Pathogen/pest resistance: Plants of the new *Verbena* have not been observed to be resistant to pathogens and pests common to *Verbenas*.

It is claimed:

1. A new and distinct *Verbena* plant named 'Duemplavbu' as illustrated and described.

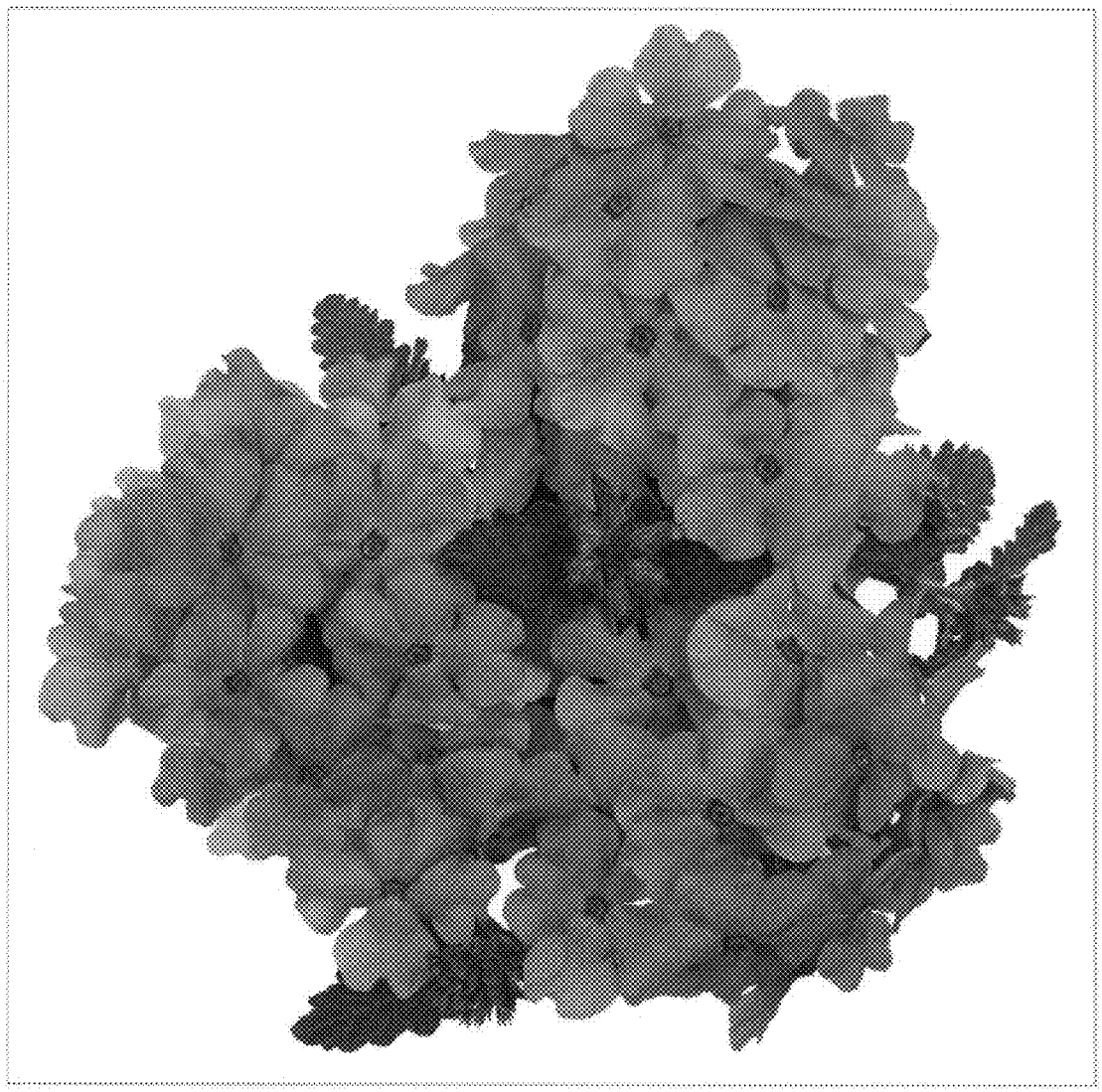

* * * * *